(12) United States Patent
Forrer et al.

(10) Patent No.: US 6,347,460 B1
(45) Date of Patent: Feb. 19, 2002

(54) DEVICE FOR GAUGING AND VERIFYING THE PRECISION OF SURGICAL INSTRUMENTS

(75) Inventors: Ruth Forrer, Möhlin; José L. Scherrer, Densingen, both of (CH)

(73) Assignee: Synthes, Paoli, PA (US)

( * ) Notice: Subject to any disclaimer, the term of this patent is extended or adjusted under 35 U.S.C. 154(b) by 39 days.

(21) Appl. No.: 09/627,064

(22) Filed: Jul. 27, 2000

Related U.S. Application Data

(63) Continuation-in-part of application No. PCT/CH98/00030, filed on Jan. 27, 1998.

(51) Int. Cl.[7] .......................... B23Q 17/20; B23Q 17/22
(52) U.S. Cl. ..................... 33/626; 33/1 CC; 700/175; 700/303; 702/94; 702/150; 128/920
(58) Field of Search .................. 33/1 CC, 1 MP, 33/503, 626, 613; 700/225, 175, 303; 702/94, 95, 150; 128/920

(56) References Cited

U.S. PATENT DOCUMENTS

| | | | |
|---|---|---|---|
| 4,403,860 A | * | 9/1983 | Pryor .......................... 33/626 |
| 4,815,218 A | * | 3/1989 | Gordy ......................... 33/628 |
| 5,323,543 A | | 6/1994 | Steen et al. ................... 33/626 |
| 5,483,961 A | | 1/1996 | Kelly et al. ............... 128/653.1 |
| 5,617,857 A | | 4/1997 | Chader et al. ........... 128/653.1 |
| 5,768,138 A | * | 6/1998 | Ruotolo ...................... 700/175 |
| 5,884,239 A | * | 3/1999 | Romanik, Jr. ................ 702/150 |
| 5,987,960 A | | 11/1999 | Messner et al. .............. 73/1.79 |
| 6,131,296 A | * | 10/2000 | Fäger ......................... 33/1 CC |
| 6,253,160 B1 | * | 6/2001 | Hanseder ..................... 702/95 |

FOREIGN PATENT DOCUMENTS

| | | |
|---|---|---|
| WO | WO 97/29683 | 8/1997 |
| WO | WO 97/29710 | 8/1997 |

* cited by examiner

*Primary Examiner*—Diego Gutierrez
*Assistant Examiner*—Madeline Gonzalez
(74) *Attorney, Agent, or Firm*—Pennie & Edmonds LLP

(57) ABSTRACT

A device for gauging and verifying the precision of surgical instruments is provided. The device includes a holder, at least one instrument, and a carousel having at least one cavity configured and dimensioned in the shape of the at least one instrument. The carousel is rotatably coupled to the holder. Markers or sensors for emitting or receiving signals are fitted to at least two of the holder, the carousel and the instrument, and allow determination of spatial information thereof. The spatial information is calibrated by inserting the at least one instrument in its respective cavity in the carousel and determining any change in dimensions from the instrument's first set of dimensions upon manufacture and its new set of dimensions following use.

12 Claims, 2 Drawing Sheets

DEVICE FOR GAUGING AND VERIFYING THE PRECISION OF SURGICAL INSTRUMENTS

CROSS-REFERENCE TO RELATED APPLICATIONS

This application is a continuation-in-part of the U.S. National Stage designation of co-pending International Patent Application PCT/CH98/00030, filed Jan. 27, 1998, the entire content of which is expressly incorporated herein by reference thereto.

FIELD OF THE INVENTION

The present invention relates to a device for gauging and verifying the precision of surgical instruments. More particularly, the present invention relates to a calibration system for computer-assisted surgery that accounts for deviations in surgical instrument dimensions from predetermined values.

BACKGROUND OF THE INVENTION

The medical sciences have been revolutionized through the widespread introduction of digital imaging technologies such as ultrasonography, computer-assisted tomography (CT scanning), and magnetic resonance imaging (MRI). Especially in orthopedic and traumatologic applications, three-dimensional visualization employing these image-acquisition systems has become an important tool for physicians.

Advances in three-dimensional imagery applications have now been deployed in pre-operative, operative, and post-operative settings, providing practitioners with a variety of tools for simulation and/or computer-assisted guidance of medical procedures tailored to the actual anatomy of a given patient. For example, computer-based rendering of bone geometry—such as contours and volume characteristics—as well as bone surface features can provide the surgeon with a visual representation of an injury to a bone or joint. Such renderings can provide valuable insight with respect to strategies for invasive surgery. Furthermore, the three-dimensional imaging systems can provide a means for simulating surgical procedures, such as the virtual manipulation of bone sections. The simulations may also be useful in the shaping of bone and joint implants, or other anatomical modeling applications.

Three-dimensional imaging technologies have been introduced primarily for pre-surgery simulation and for computer-assisted navigation of surgical instruments with respect to a patient during surgical procedures. Particularly in applications involving the latter, it is desirable to precisely determine the position and orientation of the surgical instrument relative to a spatial reference system. The introduction of an accurate surgical aid of this type to an operating room setting advantageously allows a surgeon to dynamically observe the position of a surgical instrument with respect to a patient. Through the use of a computer processor, monitor, and an appropriate software module, it is possible to predict and display intended trajectories for surgical instruments, in real time, as a function of the instruments' current orientations. Thus, surgical instruments may be precisely positioned without extensive preoperative planning. However, the guidance software can also allow the surgeon to compare an instrument path that was planned prior to an operation with the current position of the instrument, as well as the path resulting from that instrument position and orientation at any given time. Thus, in practice, an instrument path planned prior to surgery may be followed during surgery to guide the movement of an instrument.

A vast array of surgical instruments can be adapted for computer-assisted surgery, including without restriction such common tools as drills, spoons, scissors, forceps, and probes. In order to facilitate the detection of an instrument's position in a three-dimensional coordinate measuring system, the instrument is provided with markers or sensors for emitting or receiving electromagnetic waves, sound waves or magnetic fields. Each of these approaches to registering positional data presents limitations or challenges to achieving repeatable and thus reliable accuracy. Ultrasound measurements, for example, may be undertaken in an air environment, and thus are subject to changes in the physical characteristics of air which show significant variation as a function of temperature, pressure and relative humidity. Thus, when using ultrasonic registration, such external factors must be constantly measured so that deviations in the measurements may be continuously compensated. Without this monitoring, significant positioning errors may occur. Such compensation for external factors that effect registration is also necessary for magnetic-field measurement. For example, adjustments may be required to account for interference fields emanating, for instance, from display monitors, computers or electric motors, as well as non-permeable materials in the magnetic field such as metal objects moving within the magnetic field.

Systems for medical diagnosis and treatment that use reference field transducers and medical probes with probe field transducers to detect the position, orientation, or both of the probe within the body of a subject are disclosed in WO 97/29683 to Acker et al. A device that incorporates a frame which can be firmly aligned with an operating table is provided with fiducial gauging receptacles for a surgical probe. Markers are attached to a probe and the frame, and the frame can be locked in position relative to a patient. Provisions are included for transmitting, for example, a magnetic field between the markers on the probe and those on the frame. Sensors are used to detect any such field, and a processor is used to process the detected-field data and determine the position of the probe relative to the markers on the frame. The frame includes catheter calibration receptacles, positioned in known locations relative to transducer mounts. Before a probe carrying catheter is inserted into the body of a subject, the catheter is calibrated by placing the distal tip thereof, which carried the probe, in each of the receptacles in turn, and comparing the respective known position of the receptacle with position information derived from signals generated by position information generating means in the catheter. The drawback of this earlier design lies in the fact that the gauging receptacles can be used for one single probe only.

There is a need for a device for the precise gauging and accuracy verification of surgical instruments. In particular, there is a need for a device that can detect any deformation or wear of surgical instruments by a comparison with factory calibration. More particularly, there is a need for a device that can detect my change in the length of a surgical instrument such as a needle or drill bit.

SUMMARY OF THE INVENTION

The invention relates to a device for gauging and verifying the precision of instruments comprising a holder, at least one instrument having a first set of dimensions upon manufacture and a new set of dimensions following use, and a carousel having at least one cavity configured and dimensioned in the shape of the at least one instrument. The carousel is rotatably coupled to the holder. At least two of the holder, the carousel and the instrument are fitted with markers or sensors for emitting or receiving signals for determining spatial information thereof. The spatial information is calibrated by inserting the at least one instrument in its respective cavity in the carousel and determining any change in dimensions from the first set of dimensions to the second set of dimensions.

Preferably, the carousel is rotatably coupled to the holder with a longitudinal member, and the device can include a computer processor for processing and calibrating the spatial information. The spatial information can be positional and orientational data.

In a preferred embodiment, the signals are electromagnetic waves. The signals can be generated by optical light sources, light emitting diodes, or infrared light emitting diodes. The signals also can be carried by fiber optics illuminated by a light source. In other preferred embodiments, the signals can be acoustic waves or magnetic fields.

The invention also relates to a method for gauging and verifying the precision of instruments, the method including the steps of: providing at least one of a holder and carousel, and at least one instrument with markers or sensors for emitting or receiving signals; inserting the at least one instrument in a carousel having at least one cavity, the cavity precisely configured and dimensioned in an as-manufactured shape of the at least one instrument so that the instrument in its as-manufactured shape is disposed at a first spatial location; rotatably coupling the carousel to a holder; determining a new spatial location for the at least one instrument in the cavity; comparing the first spatial location with the new spatial location to determine any change in dimensions of the instrument from the as-manufactured shape; and generating calibration data to account for the change in dimensions.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF PREFERRED EMBODIMENTS

Figure 1:
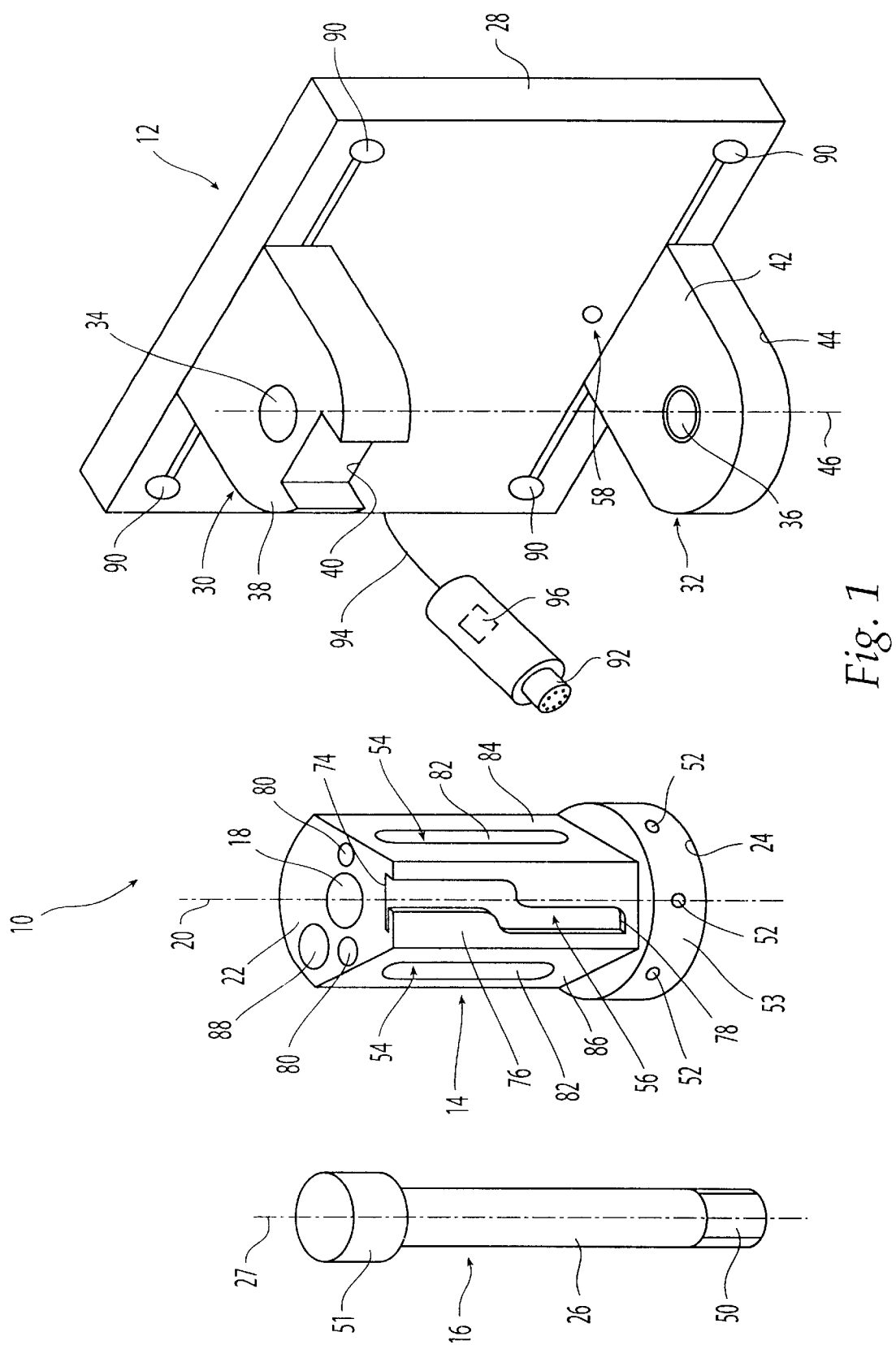
FIG. 1 shows an exploded perspective view of one embodiment of the calibration device according to the present invention.
Figure 2:
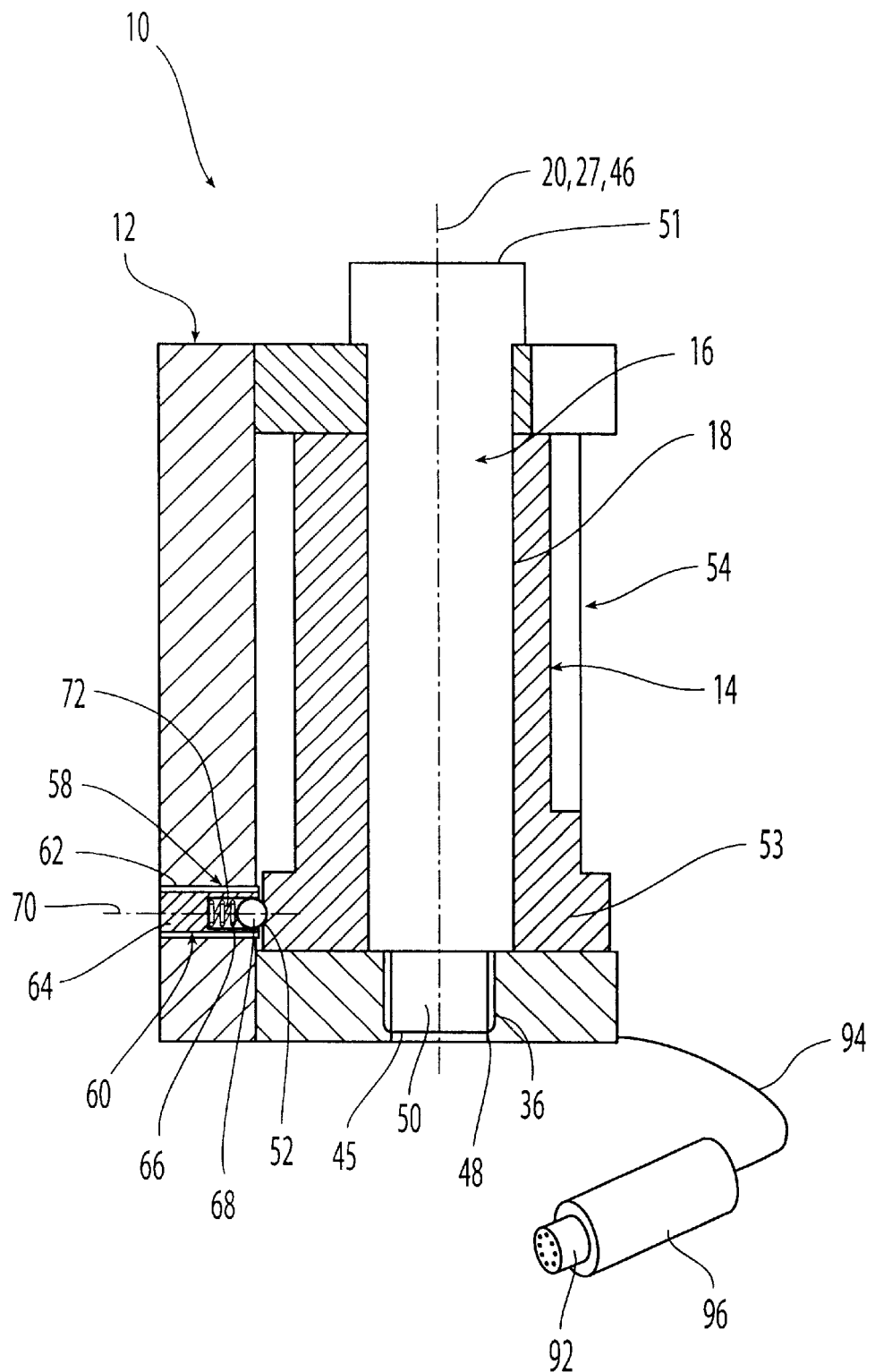
FIG. 2 shows a cross-sectional view of the calibration device of FIG. 1.

A calibration device formed in accordance with the principles of the present invention is shown in FIGS. 1 and 2. Calibration device 10 includes a holder 12, a carousel unit 14, and a longitudinal member 16 for locating carousel unit 14 with respect to holder 12. In a preferred embodiment, carousel unit 14 has a generally cylindrical shape, and includes a bore 18 having a longitudinal axis 20 and is configured to receive longitudinal member 16. Bore 18 connects upper surface 22 and lower surface 24. Preferably, longitudinal member 16 is a bolt that is configured to be received within bore 18. Shaft portion 26 of longitudinal member 16 has longitudinal axis 27 and an outer diameter that closely matches the inner diameter of bore 18, so that longitudinal member 16 provides a bearing surface along which carousel unit 14 rotates. Thus, a tight tolerance is preferably maintained between the outer diameter of longitudinal member 16 and the inner diameter of bore 18 so that there is a minimal radial clearance between them.

Holder 12 preferably includes a support 28 with brackets 30, 32 secured thereto having bores 34, 36 respectively. Bore 34 connects upper surface 38 and lower surface 40 of bracket 30, while bore 36 of bracket 32 may only partially extend from upper surface 42 toward lower surface 44, terminating at an intermediate surface 45. Bores 34,36 are preferably coaxially disposed about longitudinal axis 46. In a preferred embodiment, bore 36 includes internal threading 48, as shown in FIG. 2. Internal threading 48 advantageously has a profile designed to accommodate external threading, not shown, on lower portion 50 of longitudinal member 16. In an alternate embodiment, bore 36 and lower portion 50 instead may have smooth surfaces with internal and external diameters, respectively, that have a minimal radial clearance between them.

When calibration device 10 is assembled, carousel unit 14 is placed between brackets 30, 32 of holder 12 such that longitudinal axes 20,46 are coaxial, and longitudinal member 16 is inserted through bores 34, 18, and 36. Thus, longitudinal axis 27 of longitudinal member 16 is also coaxially located with respect to longitudinal axes 20, 46. To facilitate the assembly process, longitudinal member 16 preferably includes a knurled rim, screwdriver slot, and/or hex-socket on upper portion 51 to ease manipulation of longitudinal member 16. These features also facilitate the use of a wrench or other tools for threading and unthreading longitudinal member 16 when inserted through the bores.

It will be appreciated that various carousel units 14 may be used with holder 12. This is particularly advantageous, for example, because carousel units 14 may be loaded with selections of surgical tools that are appropriate for different surgical procedures. Thus, each surgeon using an operating room may choose to install a different carousel unit 14 in red holder 12 to accommodate the particular needs of the surgery to be performed. Alternatively, a surgeon may require that a diverse array of surgical tools be available during a given procedure, and a number of carousels may be available for the surgeon's use. The tight tolerance that is preferably maintained between the outer diameter of longitudinal member 16 and the inner diameter of bores 18 in carousels 14 permits the accurate use of many carousels 14 with the same holder 12. Such an interchangeable arrangement facilitates efficient use of calibration device 10, each holder potentially including different cavity configurations for housing surgical instruments as will be discussed below.

In a preferred embodiment, carousel unit 20 is provided with indentations 52 which are located in the vicinity of and correspond to each cavity 54, 56 in carousel unit 20. The cavities 54, 56 can be precisely aligned relative to the calibration device 10. Holder 12 is provided with a spring-loaded detent 58, which extends from holder 12 to engage an indentation 52 in lower portion 53 of carousel unit 20. Referring to FIG. 2, spring-loaded detent 58 is preferably a compression-spring unit 60 that has a cylindrical outer shape with threading. Unit 60 is installed in a like-threaded, tapped hole 62 in holder 12, and includes a screw body 64, a compression spring 66, and a ball 68. Ball 68 and spring 66 are mounted coaxially about axis 70 in a recess 72 formed in screw body 64, such that ball 68 protrudes partway out of recess 72. In an alternate embodiment, spring-loaded detent 58 includes a bevel-tip pin instead of ball 68.

When carousel unit 20 is installed in holder 12 using longitudinal member 16, the carousel unit may be rotated about axes 20, 27, 46. Indentations 52 are aligned to intersect axis 70 on which ball 68 is disposed, such that ball 68 may seat in an indentation 52 when carousel unit 20 has been rotated to align ball 68 with indentation 52. Because ball 68 is mounted on spring 66, the spring 66 is naturally compressed as the ball is forced into recess 71 when an indentation 52 is not aligned with ball 68. Although the amount of compression of spring 66 is decreased when ball 68 seats in an indentation 52, spring 66 still provides enough force to maintain the engagement of ball 68 with an indentation 52 to releasably lock carousel unit 20 in a desired and precise orientation with respect to holder 12. Advantageously, because spring-loaded detent 58 allows carousel unit 20 and its associated cavities to be precisely positioned by click-stop action, a number of surgical instruments may be housed in carousel unit 20 in a readily accessible fashion such that the calibration of each instrument's dimensions may be separately achieved. In addition, because carousel unit 20 can be precisely positioned, each surgical instrument housed in a cavity therein can be located at a precisely known, spatially defined position.

Cavities 54, 56 in carousel unit 20 are precisely machined to accommodate a surgical instrument of a given geometry. The contour of the cavities 54, 56 is formed so that it exactly mimics the shape of the surgical instrument to within a known, high tolerance. Each carousel unit 20 is provided on its outer surface with indentations 52 that each correspond to a cavity in carousel unit 20, and further permit the click-stop detent on the holder, when engaged in an indentation 52, to releasably hold the corresponding cavity in a precisely defined position and orientation relative to the calibration device 10. Cavity 56, for example, houses an instrument that fits into slot 74 in upper surface 22 of carousel unit 20. Cavity 56 is open on side 76, permitting a user to verify that an instrument inserted therein contacts the cavity bottom 78 and/or other surfaces of cavity 56. Alternatively, a cavity 54 may be precisely machined in carousel unit 20 so that a surgical instrument may be housed therein by inserting the instrument into cavity 54 through a hole 80. Cavities 54 may be open along a side 84 or 86 to permit a surgeon to verify that an instrument housed therein has been inserted properly. Access to other cavities machined into carousel unit 20, not shown, may be provided by holes of other sizes and/or shapes, such as hole 88 in upper surface 22.

Due to the instrument-matching contour of each cavity 54, 56, each surgical instrument placed in its corresponding cavity 54, 56 is retained in a precisely defined position and orientation with respect to housing 12 and overall with respect to calibration unit 10. Because of the precisely defined geometry of each cavity, surgical instruments housed in the cavities may be precisely gauged in terms of their position and orientation, even when such instruments do not have an unusual feature or a pointed end.

Each surgical instrument housed in a cavity 54, 56 is provided with markers or sensors for emitting or receiving signals such as electromagnetic waves, sound waves or magnetic fields. In a preferred embodiment, each surgical instrument, not shown, is provided with at least three light emitting diodes (LEDs). It is desirable to have at least three such markers or sensors so that triangulation principles may be used to gauge and verify dimensions and/or measurements, as is known in the art. Similarly, holder 12 is equipped with at least three LEDs 90 that permit the detection of the exact location and orientation of the device by means of a positional measuring system. Preferably, the light waves emitted by LEDs 90 are detected by at least two sensors that are part of an optical coordinate-measuring system (not shown). A positional measuring unit appropriate for this application is the three-dimensional motion-sensing system OPTOTRAK 3020, which is commercially available from Northern Digital Inc. The signals received by the optical sensors are processed by a computer, using techniques known in the art such as run-length measurements, interferometry, or videogrammetry, so that the measured values permit the determination of the exact location and orientation of calibration device 10 and particularly holder 12. The LEDs provided on a surgical instrument are similarly utilized. In alternate embodiments, instead of utilizing the aforementioned optical light sources, other devices may be used such as reflectors illuminated by external light sources, infrared light emitting diodes (IREDs), or fiber optics illuminated by a light source.

Thus, alternate embodiments of calibration device 10 may employ other means for detecting location and orientation, such as transmitters emitting selected wavelengths of electromagnetic waves. While optical light sources may be used, other systems may be acoustic wave-based and rely upon transmitters emitting sound waves and receivers in the form of microphones. Induction coils may also be used in combination with Hall-effect detectors. The use of such transmitters and receivers facilitates the rapid and accurate gauging of different surgical instruments in terms of their spatial position and orientation, which in turn permits the rapid correction of measuring errors when using suitably equipped surgical instruments. Such correction may be made before, during, or after medical procedures that require the surgical instruments.

In a preferred embodiment, a plug connector 92 on computer interconnecting cable 94 contains an erasable electronic memory device 96 that stores the positional and orientational data for calibration device 10. Preferably, electronic memory device 96 is an erasable programmable read-only memory (EPROM). Electronic memory device 96 may be used in conjunction with controller software operating on appropriate computer hardware.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, only two transmitters and two receivers may be necessary for calibrating some devices. Furthermore, the rotation and alignment of the carousel unit about the holder may be achieved using an alternative mechanism that does not provide click-stop action, such as the formation of interlocking tongue and groove patterns on the carousel unit and holder. In addition, a holder that accommodates multiple carousels at one time may be provided. The calibration system may also be used in other industries that require the gauging and verification of instruments, such as the aerospace, microelectronics, automotive, and textile sectors. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for gauging and verifying the precision of instruments, the device comprising:

a holder;

at least one instrument having a first set of dimensions upon manufacture and a new set of dimensions following use; and a carousel having at least one cavity configured and dimensioned in the shape of the at least one instrument, the carousel rotatably coupled to the holder, wherein at least two of the holder, the carousel and the instrument are fitted with markers or sensors for emitting or receiving signals for determining spatial information thereof, and wherein the spatial information is calibrated by inserting the at least one instrument in its respective cavity in the carousel and determining any change in dimensions from the first set of dimensions to the second set of dimensions.

2. The device of claim 1, further including a computer processor for processing and calibrating the spatial information.

3. The device of claim 2, wherein the carousel is rotatably coupled to the holder with a longitudinal member.

4. The device of claim 2, wherein the spatial information is positional and orientational data.

5. The device of claim 2, wherein the signals are electromagnetic waves.

6. The device of claim 2, wherein the signal are generated by optical light sources.

7. The device of claim 2, wherein the signals are generated by light emitting diodes.

8. The device of claim 2, wherein the signals are generated by infrared light emitting diodes.

9. The device of claim 2, wherein the signals are carried by fiber optics illuminated by a light source.

10. The device of claim 2, wherein the signals are acoustic waves.

11. The device of claim 2, wherein the signals are magnetic fields.

12. A method for gauging and verifying the precision of instruments, the method including the steps of:

providing at least one of a holder and carousel, and at least one instrument with markers or sensors for emitting or receiving signals;

inserting the at least one instrument in a carousel having at least one cavity, the cavity precisely configured and dimensioned in an as-manufactured shape of the at least one instrument so that the instrument in its as-manufactured shape is disposed at a first spatial location;

rotatably coupling the carousel to a holder;

determining a new spatial location for the at least one instrument in the cavity;

comparing the first spatial location with the new spatial location to determine any change in dimensions of the instrument from the as-manufactured shape, and generating calibration data to account for the change in dimensions.

* * * * *

UNITED STATES PATENT AND TRADEMARK OFFICE
CERTIFICATE OF CORRECTION

PATENT NO. : 6,347,460 B1  Page 1 of 1
DATED : February 19, 2002
INVENTOR(S) : Forrer et al.

It is certified that error appears in the above-identified patent and that said Letters Patent is hereby corrected as shown below:

Title page,
Assignee, replace "Synthes" with -- Synthes (USA) --;

Column 7,
Line 25, replace "signal" with -- signals --.

Signed and Sealed this

Twenty-third Day of April, 2002

Attest:

JAMES E. ROGAN
*Attesting Officer*     *Director of the United States Patent and Trademark Office*